United States Patent [19]

Mellul et al.

[11] Patent Number: 6,132,736
[45] Date of Patent: Oct. 17, 2000

[54] COSMETIC COMPOSITION BASED ON A MICRODISPERSION OF WAX COMPRISING A LIPOPHILIC ORGANOFLUORINE COMPOUND

[75] Inventors: Myriam Mellul, L'Hay les Roses; Bertrand Piot, La Garenne-Colombes, both of France

[73] Assignee: L'Oreal, Paris, France

[21] Appl. No.: 08/293,099

[22] Filed: Aug. 19, 1994

[30] Foreign Application Priority Data

Aug. 20, 1993 [FR] France .................... 93 10160

[51] Int. Cl.[7] .................. A61K 7/48; A61K 7/032
[52] U.S. Cl. ............... 424/401; 424/70.1; 424/70.2; 424/70.7; 424/70.11
[58] Field of Search ................. 424/401, 70.1, 424/70.11, 70.2, 70.7

[56] References Cited

U.S. PATENT DOCUMENTS

| | | | |
|---|---|---|---|
| 3,952,066 | 4/1976 | Glickman et al. | 260/615 |
| 5,358,719 | 10/1994 | Mellul et al. | 424/497 |

FOREIGN PATENT DOCUMENTS

| | | |
|---|---|---|
| 394078 | 8/1990 | European Pat. Off. . |
| 0394078 | 10/1990 | European Pat. Off. . |
| 0557196 | 8/1993 | European Pat. Off. . |
| 2052579 | 5/1972 | Germany . |
| 62-223105 | 3/1986 | Japan . |
| 9311103 | 6/1993 | WIPO . |
| WO 93/11103 | 6/1993 | WIPO . |

OTHER PUBLICATIONS

Mori Kenji, "Multi-Phase Emulsion Cosmetic", Patent Abstracts of Japan, vol. 12, No. 84 (C-482) Mar. 1988.

*Primary Examiner*—Jyothsan Venkat
*Attorney, Agent, or Firm*—Nixon & Vanderhye P.C.

[57] ABSTRACT

Cosmetic composition or cosmetic composition carrier comprising an aqueous microdispersion of particles containing at least one wax, the said particles being solid up to a temperature equal to at least −30° C., the said particles containing, in addition, a lipophilic hydrofluorocarbon organic compound such that the proportion of the number of fluorine atoms with respect to the total number of fluorine and hydrogen atoms linked to the carbon atoms in the molecule of the said compound is equal to at least 10% and is not greater than 90%.

Application of the said composition, in particular, for making up eyelashes or hair care.

24 Claims, No Drawings

COSMETIC COMPOSITION BASED ON A MICRODISPERSION OF WAX COMPRISING A LIPOPHILIC ORGANOFLUORINE COMPOUND

The present invention relates to a composition comprising an aqueous dispersion of wax particles and at least one lipophilic organofluorine compound, the dispersion being an aqueous microdispersion of at least one wax. Such a composition is usable, in particular, as a cosmetic composition.

It is known that waxes, the use of which in cosmetology is very ancient, are natural (animal or plant) or synthetic substances, solid at room temperature (21° C.), which are insoluble in water and soluble in oils and which are capable of forming water-repellent films. Regarding the definition of waxes and their uses in cosmetology, there may be mentioned, for example, P. D. Dorgan, Drug and Cosmetic Industry, December 1983, pages 30–33, and Handbook of Cosmetic Science, H. W. Hibbot ed., Pergamon Press, Oxford (1963) page 60. In hair-care preparations, the most traditional use is that of semi-solid preparations called hair pomades or solid brilliantines. In such compositions, the waxes are used mixed, in particular, with large proportions of various oils; see, for example, E. W. Flick, "Cosmetic and Toiletry Formulations" Ed. Noyes Publication-New Jersey-USA (1984) pages 271–288.

It is known, moreover, that it is possible to obtain microemulsions with some oils, and with some waxes microdispersions which are stable and can be diluted indefinitely in water without aggregation or sedimentation of the suspended particles. The microdispersions of wax are obtained by melting the wax in the presence of a surfactant, and optionally of a part of the water, followed by gradual addition of hot water with stirring. The intermediate formation of a water-in-oil type emulsion is observed, followed by a phase inversion, an oil-in-water type emulsion finally being obtained. On cooling, a stable microdispersion of solid colloidal wax particles is obtained; see, for example, "Microemulsions Theory and Practice", L. M. Prince Ed., Academic Press (1977) pages 21–32.

Microdispersions of waxes may be used, for example, as dressing agents (self-lustering products) for leather articles, floor coverings (in particular made of plastic) or furniture, or alternatively as textile conditioning agents.

In Patent Applications EP-A-394,078, EP-A-446,094 and EP-A-477,053, microdispersions of waxes intended for application to hair have also been described.

These microdispersions of waxes yield, after application, waxy films possessing a certain rigidity. It is desirable for these rigidity properties to be modified in order to endow the film with better plasticity.

It was discovered that the addition of lipophilic hydrocarbon-based organofluorine compounds to a microdispersion of wax enabled the wax microparticles to be plasticized.

Thus, it was discovered that, after the addition of certain lipophilic organofluorine compounds, compositions based on aqueous microdispersions of wax possess good film-forming and plastic properties, which prove advantageous, in particular, for application to eyelashes, to hair and also to textile fibres, and for application to leathers, floor coverings or furniture, for which the lustering effect obtained is improved and is longer-lasting.

Whereas perfluorinated lipophilic organofluorine compounds are not compatible with microdispersions of waxes (they do not give homogeneous solid microparticles with waxes), it was discovered that, surprisingly, partially fluorinated lipophilic organofluorine compounds are compatible with microemulsions of waxes, the properties of which they improve, as mentioned above.

In one of its aspects, the subject of the present invention is hence a composition, and in particular a cosmetic composition or a cosmetic composition carrier, comprising an aqueous microdispersion of particles containing at least one wax and at least one lipophilic organofluorine compound.

The compositions of the invention are free from perfluorinated organofluorine compounds.

The subject of the invention is, in particular, a composition comprising an aqueous microdispersion of particles containing at least one wax, the said particles being solid up to a temperature equal to at least 30° C., characterized in that the said particles contain, in addition, a lipophilic hydrofluorocarbon organic compound such that the proportion of the number of fluorine atoms with respect to the total number of fluorine and hydrogen atoms linked to the carbon atoms in the molecule of the said compound is equal to at least 10% and is not greater than 90%.

The particles of the microdispersion of wax are less than 1 μm, and preferably less than 0.5 μm, in average size.

These particles consist essentially of the wax or mixture of waxes and the lipophilic hydrocarbon-based organofluorine compound. The particles of the micro-dispersion can, in addition, contain, in less abundant proportions, oily or pasty fatty additives, one or more surfactants and one or more common fat-soluble active ingredients, as will be specified below.

The composition generally contains from 1 to 40% by weight of waxes, especially 5 to 30%, and a sufficient amount of at least one emulsifier. The amount of emulsifier is an amount which is sufficient to enable a microdispersion of waxes as is defined above to be obtained. This sufficient amount may be determined in each case by routine experiments.

The melting point of the wax or mixture of waxes is preferably between 50° C. and 100° C.

The wax or waxes constituting the waxy mixture are chosen, in particular, from carnauba wax, candelilla wax and esparto wax, and mixtures thereof.

Besides the waxes mentioned above, the mixture of waxes can also contain one or more of the following waxes or families of waxes:

paraffin wax;

ozokerite;

vegetable waxes such as olive-tree wax, rice wax, hydrogenated jojoba wax or absolute flower waxes such as essential wax of blackcurrant flower, sold by the company Bertin (France);

animal waxes such as beeswax or modified beeswaxes (Cerabellina);

other waxes or waxy starting materials: marine waxes such as that sold by the company Sophim under the reference M82, natural or synthetic ceramides or polyethylene waxes.

The vegetable waxes carnauba wax (extracted from *Copernica cerifera*), candelilla wax (extracted from *Euphorbies cerifera* and *Pedilantus pavonis*) and esparto wax (extracted from *Stipa tenacissima*) are commercial products. Ceramides are the main lipids constituting the intercorneocytic spaces of the stratum corneum. They are described especially by Downing in Science, 1982, Vol. 18, p. 1261–2. Synthetic analogues are also known, such as the HO3 ceramides sold by the company Cosmind. In the mixture of waxes, the carnauba and/or candelilla and/or esparto wax preferably represents at least 20%, and especially at least 50%, by weight relative to the total weight of the mixture of waxes.

In the microparticles of the composition according to the invention, the wax and the lipophilic organofluorine compound form a homogeneous mixture, the said organofluorine compound being soluble in the wax. In the composition of the invention, the lipophilic organofluorine compound is generally present in the proportion of 5 to 50%, and especially 10 to 30%, by weight relative to the total weight of wax.

A compound is considered here to be lipophilic if it is hydrophobic, that is to say insoluble in water and miscible with common lipids, and in particular with the waxes as are defined above. In particular, the lipophilic organofluorine compound may be chosen from those which are miscible with carnauba wax to the extent of at least 10% by weight.

The wax or mixture of waxes can contain, besides the waxes mentioned above, at least one other wax and/or at least one oil, on the understanding that the mixture of wax(es), organofluorine compound and, where appropriate, oil, must be solid up to a temperature of approximately 50° C. and must melt at a temperature below 100° C.

The mixture of waxes may hence be combined with one or more fatty (oily or pasty) additives. There may be mentioned, without implied limitation:

vegetable oils such as sunflower oil, jojoba oil, and the like, mineral oils such as liquid paraffin, fluid silicone oils of viscosity lying, in particular, between 0.65 and 100,000 centistokes (that is to say between $0.65 \times 10^{-6}$ and $0.1$ $m^2.s^{-1}$), and preferably between 5 and 5,000 centistokes (that is to say between $5 \times 10^{-6}$ and $5 \times 10^{-3} m^2.s^{-1}$), petroleum jelly, lanolin.

The mixture of oil(s) and/or pasty fatty additives can represent up to 30% (preferably at most 10%) of the weight of wax(es).

It is possible to introduce, in addition, fat-soluble active ingredients into the microparticulate waxy phase.

When they are present, the fat-soluble ingredient or ingredients represent(s) at most 30%, and preferably at most 10%, of the weight of the microparticles.

As fat-soluble ingredient(s) there may be mentioned, for example, in the case of cosmetic compositions:

UV screening agents, fat-soluble vitamins, anti-inflammatories such as β-glycyrrhetinic acid, fat-soluble plant extracts.

The organofluorine compounds which are usable in the compositions of the invention have a chemical structure principally containing a hydrocarbon skeleton in which a portion of the hydrogen atoms has been substituted by fluorine atoms. The said hydrocarbon skeleton can contain, in addition, one or more hetero atoms and one or more functional groups.

For a molecule of hydrocarbon-based organofluorine compound, a degree of substitution of the hydrogen atoms by fluorine atoms is defined in the form of the ratio:

number of fluorine atoms/(number of fluorine atoms+ number of hydrogen atoms), where only the hydrogen atoms linked to the carbon atoms of the skeleton are taken into account in the measurement in question.

For the organofluorine compounds used according to the invention, this degree of substitution does not exceed 90% and is generally between 10 and 80%. Preferably, this degree is greater than 30% and less than 60%.

The organofluorine compounds used in the compositions of the invention are, in particular, compounds corresponding to the following formula:

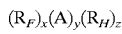

$(R_F)_x(A)_y(R_H)_z$ in which:

$R_F$ represents a fluorinated organic group having at least four carbon atoms, $R_H$ represents an unfluorinated hydrocarbon group, the said hydrocarbon group being optionally substituted and/or optionally containing one or more hetero atoms or heteroatomic groups, A represents a divalent, trivalent or tetravalent linking group, x represents the number 1, 2 or 3, y represents the number 0 or 1, z represents the number 0, 1, 2 or 3, on the understanding:

that, when y is other than zero, the sum (x+z) is equal to the valency of the linking group A, and each group $R_F$ and $R_H$ is then linked to A via a covalent bond, that, when y=0, then x=z=1 and the group $R_F$ and the group $R_H$ are then linked to one another via a covalent bond, and that, when z is equal to 0, y is other than 0.

In the above definition, hetero atoms denote, in particular, —O— or —S—; the heteroatomic groups are, for example, —SO— or —SO$_2$— groups or groups —N(R')—, R' being, in particular, a hydrogen, am alkyl or an aralkyl.

Among organofluorine compounds, there may be mentioned, in particular, those which possess one or more of the following features:

a) $R_F$ is an optionally unsaturated aliphatic or an aromatic fluorocarbon group which can contain one or more hetero atoms or heteroatomic groups and/or which can be substituted with one or more halogen atoms other than fluorine, on the understanding that the proportion, in %, of the number of fluorine atoms with respect to the total number of halogen atoms present in RF is not less than 75%;

b) $R_F$ is a perfluoroalkyl group having from 4 to 22 carbon atoms;

c) the group A is chosen from a carbon (tetravalent), a ≡CH group (trivalent), a nitrogen (trivalent), a —CO—N= group (trivalent), an —SO$_2$N= group (trivalent), a PO— (O)$_3$— group (trivalent), or a divalent group chosen from —CH$_2$—, —O—, —S—, —SO—, —SO$_2$— and —CO—NH—. It should be noted that the indication of the valencies of A, as done above, does not prejudge the structure formed by the chemical bonds with A in the compound of formula I: for example, the ≡CH group can be a group linked via 3 single covalent bonds or a group linked via a single bond and a double bond (that is to say of the —CH= type);

d) $R_H$ represents a saturated or unsaturated $C_1$–$C_{22}$ aliphatic, in particular alkyl, group, a $C_6$–$C_{10}$ aryl group or a $C_7$–$C_{15}$ aralkyl group, the said group being optionally substituted with and/or interrupted by hetero atoms or heteroatomic groups such as those defined above;

e) the groups $R_F$ and/or $R_H$ may be substituted so as to bear functions such as: alcohol, thiol, carbonyl function, carboxylic acid, ester, amine, enamine, amide, sulphonamide, sulphoxide, phosphate, and the like;

f) the lipophilic organofluorine compound corresponds to the formula (II):

$R_1$—(CH$_2$)$_n$—X—[C$_3$H$_5$(OH)]—(Y)$_p$—R$_2$ (II)

in which:

$R_1$ represents a perfluorinated alkyl radical having from 4 to 20 carbon atoms, $R_2$ represents a $C_1$–$C_{22}$ alkyl, $C_6$–$C_{10}$ aryl or $C_7$–$C_{15}$ aralkyl group, X and Y independently represent a group chosen from —O—, —S—, —SO—, —$SO_2$—, n represents a number from 0 to 4, p represents the number 0 or 1, and $C_3H_5$(OH) represents one of the groups —$CH_2$CH(OH) $CH_2$—, —CH($CH_2$OH)—$CH_2$— and —$CH_2$—CH ($CH_2$OH)—, on the understanding that X and Y cannot simultaneously represent —SO— or —$SO_2$—. The group $R_2$ can represent the features given for $R_H$ above.

Such compounds are described, in particular, in Patent Applications WO-93/11103 and EP-166.696;

g) the organofluorine compound corresponds to the formula (III):

$$R_F\text{—CH=CH—}CH_2OCH_2[C_2H_4OW] \quad \text{(III)}$$

in which:

$C_2H_4OW$ denotes —CHOH—$CH_2$W or —CHW—$CH_2$OH,

W represents —OR, —SR, —COOR, —$OC_6H_5$ or —O—$C_6H_4R^{11}$,

R represents an alkyl group having from 1 to 18 carbon atoms, $R^{11}$ represents —$CH_3$ or —OH at the ortho or para position, and $R_F$ represents a perfluorinated alkyl radical having from 4 to 20 carbon atoms.

These compounds are described, in particular, in the document DE-2,052,079;

h) the lipophilic organofluorine compound corresponds to the formula (IV):

$$R_F\text{—}CH_2\text{—}CH_2\text{—}X\text{—}CH_2\text{—}CH(Y')\text{—}Z \quad \text{(IV)}$$

in which:

$R_F$ is a perfluorinated alkyl group having from 4 to 20 carbon atoms,

X represents —O—, —S—, —SO— or —$SO_2$—, either Y' represents OH, and Z then represents —$C_6H_5$, —$CH_3$, —$CH_2$OH, —$CH_2$O—$COCH_3$, or Y' represents —$CH_2$OH and Z then represents —O—$COCH_3$.

These compounds are described, in particular, in U.S. Pat. No. 3,952,066;

i) the lipophilic organofluorine compound corresponds to the formula (V):

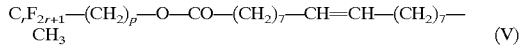

$$C_rF_{2r+1}\text{—}(CH_2)_p\text{—O—CO—}(CH_2)_7\text{—CH=CH—}(CH_2)_7\text{—}CH_3 \quad \text{(V)}$$

in which r is an integer equal to 6 or 8 and p is the number 1 or 2.

Among these compounds, there may be mentioned those marketed under the name Nofable FO by the company Nippon Oil & Co.;

j) the lipophilic organofluorine compound corresponds to the formula:

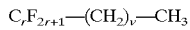

$$C_rF_{2r+1}\text{—}(CH_2)_v\text{—}CH_3$$

in which r is an integer equal to 6 or 8 and v is an integer which can vary from 12 to 16; these compounds are described by M. Napoli, IX European Symposium of Fluorine Chemistry, Leicester, September 1989;

k) the lipophilic organofluorine compound may also be chosen from those described in JP-63-002.916, which possess perfluorocarbon groups and hydrocarbon groups, the total number of carbon atoms being between 10 and 30, and the number of carbon atoms of hydrocarbon groups being equal to or greater than twice the number of carbon atoms of the perfluorocarbon groups.

The use of surfactants as emulsifiers in the preparation of microdispersions of waxes is known. The production of the microdispersion may be performed using anionic, cationic and/or nonionic surfactants, in a known manner.

The amount of surfactant present in the composition is an amount which is at least sufficient to enable a stable microdispersion of the mixture of wax and organofluorine compound to be formed. This amount may be determined in each case by routine experiments.

The weight percentage of surfactant(s) in the final composition is generally between 0.01 and 25% approximately, and can, in particular, vary from 0.1 to 10%.

The wax(es)/emulsifier(s) weight ratio can vary, for example, in the range 1 to 30, and in particular 2 to 10.

The anionic surfactants used are, in particular, salts of fatty acids (for example alkali metal salts or organic salts such as amine salts), the said fatty acids, optionally unsaturated, having, for example, from 12 to 18 carbon atoms, or alkali metal salts or salts of organic bases of alkyl sulphuric and alkylsulphonic acids having 12 to 18 carbon atoms or of alkylarylsulphonic acids in which the alkyl chain contains from 6 to 18 carbon atoms. There may also be mentioned ether sulphates, especially the sulphation products of polyalkoxylated fatty alcohols and alkylphenols in which the aliphatic chain contains from 6 to 20 carbon atoms and the polyalkoxy chain from 1 to 30 oxyalkylene, especially oxyethylene, oxypropylene or oxybutylene units.

All these anionic surfactants are well known, and several of them are commercial products.

The nonionic surfactants are, for example, polyalkoxylated and/or polyglycerolated surfactants. They are, in particular, polyalkoxylated and/or polyglycerolated fatty acids or fatty acid amides; polyalkoxylated and/or polyglycerolated fatty alcohols or alkylphenols; polyalkoxylated and/or polyglycerolated esters of fatty acids and polyols; polyalkoxylated and/or polyglycerolated 1,2- or 1,3-alkanediols or -alkenediols; and alkyl ethers of polyalkoxylated and/or polyglycerolated 1,2- or 1,3-alkanediols or -alkenediols; for example, the fatty acids or alcohols, optionally unsaturated, have 12 to 24 carbon atoms, the alkyl chain of the alkylphenols has 6 to 16 carbon atoms, the alkanediols or alkenediols have from 9 to 24 carbon atoms, the alkyl of the alkyl ethers has from 4 to 20 carbon atoms and the number of oxyalkylene units or of ($CH_2$CHOH$CH_2$O) units can range from 2 to 40.

The polyalkoxylated nonionic derivatives are, in particular, polyoxyethylenated, and where appropriate polyoxypropylenated, derivatives.

The polyalkoxylated fatty acids are commercial products, in particular the products sold under the brand name Myrj by the company Atlas.

The polyoxyethylenated esters of fatty acids and polyols for which the polyol is sorbitol are known products (polysorbate and products marketed under the brand name Tween by the company Atlas). When the polyol is glycerol, the products marketed by the company Goldschmidt under the brand name Tagat may be used.

The polyoxyethylenated fatty alcohols are also commercial products, in particular those sold under the brand name Brij by the company Atlas.

The polyglycerolated fatty alcohols, polyglycerolated alkanediols or alkenediols or alkyl ethers of polyglycerolated alkanediols or alkenediols may be prepared, for example, according to the processes described in French Patents 1,477,048, 2,025,681, 2,091,516 and 2,465,780 or according to analogous processes.

The polyglycerolated fatty acids or fatty acid amides are, in particular, described in French Patent 1,484,723, or alternatively are commercial products such as those sold under the brand name Plurol (Gattefosse) or Drewpol (Stefan Company) or Decaglyn (Nikko Chemical).

Other usable nonionic surfactants are, for example:

triglycerol alkylcarbamates of the general formula:

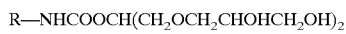

R—NHCOOCH(CH$_2$OCH$_2$CHOHCH$_2$OH)$_2$ in which R represents a saturated or unsaturated alkyl group having 10 to 20 carbon atoms. These compounds are described in Patent EP-0,420,761;

oxyethylenated or propoxylated derivatives of lanolin alcohols, of lanolin fatty acids or of mixtures thereof.

Such surfactants are marketed by the company Amerchol under the brand name Solulan.

The cationic surfactants are, in particular, quaternary ammonium derivatives such as Arquad 16-50, Arquad 18-50, Arquad T-50, Arquad 2C-75, Ethoquad c/12 and Ethoquad o/12, marketed by the company Armak Chemicals.

The use of nonionic surfactants is preferred.

It is also possible to mix the microdispersions of wax and organofluorine compound with commercial mixtures of self-emulsifying waxes containing a wax and surfactants. It is possible to use, for example, the wax marketed under the name Cire Auto Lustrante OFR by the company Tiscco, which contains carnauba and paraffin waxes, in combination with nonionic emulsifying agents, or the self-emulsifying wax marketed under the name Cerax A.O. 28/B by La Ceresine, which contains esparto wax in combination with a nonionic emulsifier. These commercial mixtures enable microdispersions of waxes to be prepared by adding water according to the process described above.

It is also possible to use commercially available ready-to-use microdispersions of waxes, such as the products of the SL slipaid series of the Daniel Products Company, or alternatively the Aquacer products of the company Cerachemie.

The microdispersions of waxes can be diluted in water without adversely affecting the stability of the microdispersion. They can hence take the form of concentrated compositions in which the proportion of the ingredients may be adjusted to a desired value by simply adding water.

The composition according to the invention can contain film-forming polymers.

Usable film-forming polymers are, in particular, those customarily used in cosmetic compositions for hair and eyelashes. They are, for example, the polymers described in the following documents: FR-1,222,944, FR-1,492,597, FR-1,564,110, FR-1,580,545, FR-2,077,141, FR-2,080,759, FR-2,137,684, FR-2-162,025, FR-2,190,406, FR-2,198,719, FR-2,265,781, FR-2,265,782, FR-2,280,361, FR-2,350,834, FR-2,357,241, FR-2,393,573, FR-2,403,076, FR-2-439,798, FR-2,529,214, BE-208,516, GB-839,805, U.S. Pat. No. 2,047,398, U.S. Pat. No. 2,102,113, U.S. Pat. No. 2,723,248, U.S. Pat. No. 3,589,978, U.S. Pat. No. 3,879,376, U.S. Pat. No. 4,031,307, U.S. Pat. No. 4,082,730, U.S. Pat. No. 4,128,631 and U.S. Pat. No. 4,131,576. The film-forming polymers may be present in the composition in the proportion of 0 to 25% by weight, and especially 2 to 15%.

The composition can also contain coloured pigments or fillers used in a standard manner.

Such coloured pigments or (uncoloured) fillers are present in a sufficient amount, generally less than 40% by weight relative to the total weight of the composition. Organic or inorganic pigments may be used, including nacreous pigments. There may be mentioned, for example, titanium dioxide, iron oxides, chromium oxide; carbon black and the various D and C red, orange or yellow organic pigments codified in the Color Index; nacreous pigments such as titanium oxide-coated mica; fillers such as talc, micas, starch, zinc and titanium oxides, calcium carbonate, powders of synthetic polymers (polyethylene, polyamide, and the like) and silicone powders.

The composition can also contain other additives such as colorants, sunscreen agents, thickening agents, perfumes, preservatives, and the like.

The compositions according to the invention can take the form of a fluid lotion or of a slightly thickened or gelled lotion. They may be used for a hair-care application, namely setting lotion, styling lotion, or for making up the eyes, namely mascara, eyeliner.

When the composition is used for making up the eyes, the viscosity of the composition is between, for example, 2.5 Pa.s and 35 Pa.s, and preferably between 3.5 and 25 Pa.s (measured using a Contraves viscometer at 200 rpm after 10 minutes of rotation).

The compositions according to the invention are obtained by formation of a microemulsion in the heated state. More specifically, these compositions are obtained by a process which is mainly characterized in that the wax and the emulsifier are heated to a temperature above the melting point of the wax and not above 100° C., optionally in the presence of a part of the water, until the wax has melted completely, in that the water, or the remainder of the water, brought to a temperature at least equal to the said temperature, is added gradually while stirring until a microemulsion of wax in a continuous aqueous phase is formed, and in that the emulsion is then allowed to cool to room temperature. A stable microdispersion of wax is obtained.

The procedure is performed with stirring and in the presence of a sufficient amount of surfactant for the microparticles of wax to be less than 1 micrometer, and preferably less than 500 nm, in size.

The organofluorine compounds and the fat-soluble ingredients, for example ceramides, are generally added to the wax before the production of the microdispersion.

The water-soluble ingredients may be added to the water used to produce the microdispersion, or to the microdispersion of wax finally obtained.

In a similar manner, the secondary ingredients possibly present in the composition are added, depending on the case, either to the starting materials or to the finished composition.

A commercial microdispersion of wax may also be added to the microdispersion obtained, as mentioned above.

The subject of the invention is also a cosmetic treatment process, characterized in that a cosmetic composition as defined above is applied to hair or to eyelashes. The application is performed in a manner known per se.

The subject of the invention is, in addition, the use of a lipophilic hydrofluorocarbon organic compound such that the proportion of the number of fluorine atoms with respect to the total number of fluorine and hydrogen atoms linked to the carbon atoms in the molecule of the said compound is equal to at least 10% and is not greater than 90%, as an additive intended for improving the properties of a cosmetic composition comprising an aqueous microdispersion of wax.

The cosmetic composition and the hydrofluorocarbon compound can be as are defined above. The fluorinated additive improves, in particular, the cosmetic properties and the plasticity of the films obtained on application of these compositions to the skin.

The examples which follow illustrate the invention.

EXAMPLES OF PREPARATION OF MICRODISPERSIONS OF WAXES

Example A

| | |
|---|---|
| Carnauba wax | 22.5 g |
| 1-(2'-F-hexylethylthio)-3-(2"-ethyl-hexyloxy)-2-propanol | 7.5 g |
| Oxyethylenated glyceryl monostearate containing 30 mol of ethylene oxide, sold under the name "Tagat S" by the company Goldschmidt | 7.5 g |
| Preservatives qs | |
| Water qs | 100.0 g |

The mixture of wax, fluorine compound and surfactants is heated to 90° C. while homogenizing with moderate stirring.

While stirring is continued, the water previously heated to 90° C. is incorporated.

The microemulsion obtained is brought back to room temperature. The preservatives are added when the temperature is in the region of 30° C.

Average diameter of the wax particles: 250 nm.

Example B

| | |
|---|---|
| Carnauba wax | 10.0 g |
| Lanolin alcohol and mixture of polyoxyethylenated fatty alcohols containing 25 mol of ethylene oxide, sold under the name "Solulan 25" by the company Amerchol | 7.5 g |
| Methyl para-hydroxybenzoate | 0.3 g |
| Fluorine compound sold under the name "Nofable FO"* by the company Nippon Oil | 2.5 g |
| Demineralized water qs | 100 g |

The microdispersion is obtained using the procedure described in Example A.

Average diameter of the wax particles: 111 nm.

*The formula of this fluorine compound is:

$C_8F_{17}-(CH_2)_2-O-CO-(CH_2)_7-CH=CH-(CH_2)_7-CH_3$

Example C

| | |
|---|---|
| Carnauba wax | 10.0 g |
| Polyoxyethylenated cetyl alcohol containing 20 mol of ethylene oxide, sold under the name "Brij 58" by the company ICI | 2.34 g |
| Fluorine compound "Nofable FO" | 2.5 g |
| Methyl para-hydroxybenzoate | 0.3 g |
| Demineralized water qs | 100.0 g |

The microdispersion is obtained using the procedure described in Example A.

Average particle diameter: 118 nm.

Example D

| | |
|---|---|
| Carnauba wax | 10.0 g |
| Cetyltrimethylammonium bromide | 3.79 g |
| Fluorine compound "Nofable FO" | 2.50 g |
| Methyl para-hydroxybenzoate | 0.3 g |
| Water qs | 100.0 g |

The microdispersion is obtained as described in Example A.

Average particle diameter: 96 nm.

Example E

| | |
|---|---|
| Carnauba wax | 18.0 g |
| "Tagat S" | 7.5 g |
| Methyl para-hydroxybenzoate | 0.2 g |
| 1-(2'-F-hexylethylthio)-2-decanol | 12.0 g |
| Water qs | 100.0 g |

The microdispersion is prepared according to the procedure of Example A.

Average particle diameter: 250 nm.

Example F

| | |
|---|---|
| Carnauba wax | 18.0 g |
| "Tagat S" | 7.5 g |
| Methyl para-hydroxybenzoate | 0.2 g |
| 1-(2'-F-octylethylthio)-2-hexanol | 12.0 g |
| Water qs | 100.0 g |

The microdispersion is prepared according to the procedure of Example A.

Average particle diameter: 195 nm.

Example G (comparative)

In this example, a perfluorinated compound is used as organofluorine agent.

| | |
|---|---|
| Carnauba wax | 10.0 g |
| "Solulan 25" | 7.5 g |
| Methyl para-hydroxybenzoate | 0.3 g |
| Perfluoropoly(methyl isopropyl ether) sold under the name "HC 25" by the company Ausimont-Monsanto | 2.5 g |
| Demineralized water qs | 100 g |

The microdispersion, which is prepared according to the process described in Example A, is not stable, which manifests itself, in particular, in a phase separation.

Example H (comparative)

A microemulsion without an organofluorine agent and having the following composition is prepared:

| | |
|---|---|
| Carnauba wax | 30 g |
| "Tagat S" | 7.5 g |
| Preservative qs | |
| Water qs | 100.0 g |

The microdispersion is obtained according to the process described in Example A.

Particle diameter: 160 nm.

Example I

| | |
|---|---|
| Carnauba wax | 21 g |
| Paraffin wax | 3 g |
| 1-(2'-F-hexylethylthio)-3-(2"-ethyl-hexyloxy)-2-propanol | 6 g |
| "Tagat S" | 7.5 g |
| Preservatives qs | |
| Water qs | 100.0 g |

The microdispersion is prepared according to the procedure of Example A.

Average particle diameter: 300 nm.

Example J

| | |
|---|---|
| Carnauba wax | 19 g |
| Modified beeswax sold under the name "Cerabellina" by the company Jan Dekker | 3 g |
| 1-(2'-F-hexylethylthio)-3-(2"-ethyl-hexyloxy)-2-propanol | 8 g |
| "Tagat S" | 7.5 g |
| Water qs | 100.0 g |

The microdispersion is prepared according to the procedure of Example A.

Average particle diameter: 250 nm.

EXAMPLES OF EYE MAKE-UP COMPOSITIONS

Procedure of Examples 1 to 4

A 2-step dilution of the initial microdispersion of wax is employed.

At room temperature, the polymer or polymers present in the formulation is/are incorporated in the microdispersion of wax with stirring, while water is optionally added, if necessary, to obtain a homogeneous preparation. The pigments are then dispersed. The formulation may be ground.

Example 1

The following composition is prepared:

| | |
|---|---|
| Microdispersion of wax according to Example A | 89.5 g |
| Black iron oxide | 5 g |
| Hydroxyethylcellulose sold under the name "Cellosize QP 4400M" by the company Amerchol | 1 g |
| | 1 g |
| Gum arabic | 1.5 g |
| Panthenol | 1.0 g |
| NaOH qs pH 7 | |
| Water | 2.0 g |

This composition is applied to eyelashes as a mascara.

On application, the eyelashes are seen to be shiny and to possess good curl and good suppleness.

Example 2

| | |
|---|---|
| Microdispersion of wax according to Example E | 86 g |
| Black iron oxide | 6 g |
| Glycerol | 3 g |
| Polyvinylpyrrolidone sold under the name "Luviskol K90" by the company BASF | 4 g |
| Poly(sodium methacrylate) | 1 g |
| NaOH qs pH 7 | |

This mascara composition is applied to eyelashes.

On application, the eyelashes are seen to be shiny and to possess good curl and good suppleness.

Examples 3 and 4 (comparative)

Mascaras of the following compositions are prepared (the contents are expressed in grammes):

| | Ex. 3 | Ex. 4 |
|---|---|---|
| Microdispersion of wax according to Example A | 88.5 | |
| Microdispersion of wax according to Example H | | 88.5 |
| Black iron oxide | 5.0 | 5.0 |
| Gum arabic | 3.0 | 3.0 |
| "Cellosize QP 400M" | 0.5 | 0.5 |
| Polyvinylpyrrolidone ("Luviskol K90" - BASF) | 1.0 | 1.0 |
| Polyquaternium-10 (CTFA name) sold under the name "Leogard GP" by the company Akzo | 1.0 | 1.0 |
| | 2 | 2 |
| NaOH qs pH 7 | | |

A jury of 10 users is asked to use the mascaras of Examples 3 and 4 whose composition they are unaware of, and to give their opinion regarding the qualities or defects of these mascaras. The mascara of Example 4 is considered by all the users to stiffen the eyelashes too strongly, while the mascara of Example 3 is considered to stiffen the eyelashes normally.

Example 5

Styling mousse

An aerosol styling mousse having the following composition is prepared:

| | |
|---|---|
| Microdispersion of wax of Example A | 22.22 g |
| Hydroxyethylcellulose crosslinked with epichlorohydrine, quaternized with trimethylamine, marketed under the name, "J.R. 400" by the company Union Carbide | 0.5 g |
| Diazolidinyl urea sold under the name "Germall II" by the company Sutton Labs | 0.1 g |
| Water qs | 100 g |
| NaOH qs pH 5.5 | |

90 g of the composition obtained are introduced into an aerosol can without a dip tube. The valve is attached, the container is sealed hermetically and 10 g of a butane/isobutane/propane propellant mixture are then introduced. The pressure in the container is 3.2 bars. It will be recalled that one bar corresponds to a pressure of $10^5$ Pa.

The styling mousse obtained is applied to wet hair. After drying, the hair possesses body, and a good shape-retention of the hairstyle is observed.

Example 6

A mascara of the following composition is prepared:

| | |
|---|---|
| Microdispersion of wax according to Example B | 93.0 g |
| Carbon black | 5.0 g |
| Hydroxypropylchitosan | 0.2 g |
| Hydroxyethylcellulose sold under the name "Cellosize QP 4400M" by the company Amerchol | 1.3 g |
| α-Bisabolol | 0.5 g |

When applied to eyelashes, this composition endows them with satisfactory shine, curl and suppleness.

What is claimed is:

1. A cosmetic composition comprising an aqueous microdispersion of wax particles comprising a lipophilic hydrofluorocarbon compound, said particles being solid up to a temperature equal to at least 30° C. and said lipophilic hydrofluorocarbon compound having at least 10% to at most 90% fluorine atoms relative to the total number of fluorine and hydrogen atoms, said composition being free of perfluorinated organofluorine compounds.

2. The composition according to claim 1 wherein said lipophilic hydrofluorocarbon compound has at least 10% to at most 80% fluorine atoms relative to the total number of fluorine and hydrogen atoms.

3. The composition according to claim 1 wherein said lipophilic hydrofluorocarbon compound has at least 30% to at most 60% fluorine atoms relative to the total number of fluorine and hydrogen atoms.

4. The composition according to claim 1 wherein said lipophilic hydrofluorocarbon compound is present in an amount ranging from 5% to 50% by weight relative to the total weight of said wax.

5. The composition according to claim 1 wherein said lipophilic hydrofluorocarbon compound is present in an amount ranging from 10% to 30% by weight relative to the total weight of said wax.

6. The composition according to claim 1 wherein said wax is present in an amount ranging from 1% to 40% by weight relative to the total weight of said composition.

7. The composition according to claim 1 wherein said wax is present in an amount ranging from 5% to 30% by weight relative to the total weight of said composition.

8. The composition according to claim 1 wherein said lipophilic hydrofluorocarbon compound has the formula (I):

$$(R_F)_x(A)_y(R_H)_z \qquad (I)$$

wherein:

$R_F$ is
(a) a fluorinated organic group having from 4 to 22 carbon atoms,
(b) a fluorinated group as defined in (a) which contains one or more functions selected from the group consisting of alcohol, thiol, carboxylic acid, ester, amine, amide, sulfonamide, sulfoxide and phosphate, or
(c) a fluorocarbon group as defined in (a) or (b) substituted by at least one halogen atoms other than fluorine, with the proviso that the number of fluorine atoms with respect to the total number of halogen atoms present in $R_F$ is not less than 75%, $R_H$ is
(d) a hydrocarbon group selected from the group consisting of $C_1$–$C_{22}$ aliphatic, $C_6$–$C_{10}$ aryl and $C_7$–$C_{15}$ aralkyl,
(e) a hydrocarbon group as defined in (d) containing one or more functions selected from the group consisting of alcohol, thiol, carboxylic acid, ester, amine, amide, sulfonamide, sulfoxide and phosphate, or
(f) a hydrocarbon group as defined in (d) or (e) interrupted by at least one heteroatom or heteroatomic group selected from the group consisting of —O—, —S—, —SO—, —SO$_2$— and —N(R'), wherein R' is selected from the group consisting of hydrogen, alkyl and aralkyl, A is a linking group, x is 1, 2 or 3, y is 0 or 1, and z is 0, 1, 2 or 3, the provisos that y is 1, the sum (x+z) is equal to the valence of A, y is 0, x and z are 1, and z is 0, y is 1.

9. The composition according to claim 8 wherein $R_F$ is an optionally unsaturated aliphatic or aromatic fluorocarbon group, optionally substituted with at least one halogen other than fluorine, with the proviso that not less than 75% of the halogen atoms on $R_F$ are fluorine atoms.

10. The composition according to claim 8 wherein A is selected from the group consisting of carbon, nitrogen, methylidyne, —CO—N═, —SO$_2$N═, PO(O)$_3$, —CH$_2$—, O, S, SO, SO$_2$, and —CONH—.

11. The composition according to claim 8 wherein $R_F$ is a perfluoroalkyl group having 4 to 22 carbon atoms, and z is 1, 2 or 3.

12. The composition according to claim 8 wherein $R_H$ is selected from the group consisting of an alkyl group of 1 to 22 carbon atoms, an aryl group of 6 to 10 carbon atoms and an aralkyl group of 7 to 15 carbon atoms.

13. The composition according to claim 1 wherein said lipophilic hydrofluorocarbon compound has the structure of formula (II):

$$R_1-(CH_2)_n-X-[C_3H_5(OH)]-(Y)_p-R_2 \qquad (II)$$

wherein:
R₁ is a perfluorocarbon alkyl radical of 4 to 20 carbon atoms,
R₂ is selected from the group consisting of $C_1$–$C_{22}$ alkyl, $C_6$–$C_{10}$ aryl and $C_7$–$C_{15}$ aralkyl,
X and Y each independently represent a group selected from the group consisting of —O—, —S—, —SO—, and —SO₂—,
n is 0, 1, 2, 3, or 4,
p is 0 or 1,
and C₃H₅ (OH) is selected from the group consisting of —CH₂CH(OH)CH₂—, —CH(CH₂OH)—CH₂— and —CH₂CH(CH₂OH)—, with the proviso that X and Y cannot simultaneously be —SO— or —SO₂—.

14. The composition according to claim 1 wherein said lipophilic hydrofluorocarbon compound has the structure of formula (IV):

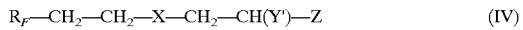

wherein:
R_F is a perfluorinated alkyl radical of 4 to 20 carbon atoms,
X is —O—, —S—, —SO—, and —SO₂—,
and either
Y' is OH and Z is —C₆H₅, —CH₃, —CH₂OH or —CH₂O—COCH₃, or
Y' is —CH₂OH and Z is —O—COCH₃.

15. The composition according to claim 1 wherein said lipophilic hydrofluorocarbon compound has the structure of formula (V):

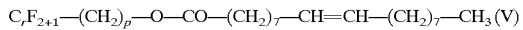

wherein:
r is 6 or 8 and p is 1 or 2.

16. A process for the treatment of the hair or eyelashes comprising applying the composition according to claim 1 to said hair or eyelashes.

17. A process for improving the plasticity of a cosmetic microdispersion containing a wax, comprising adding a lipophilic hydrofluorocarbon compound to said wax microdispersion, said lipophilic hydrofluorocarbon compound having at least 10% to not more than 90% fluorine atoms relative to the total number of fluorine and hydrogen atoms, said wax microdispersion being free of perfluorinated organofluorine compounds.

18. A cosmetic composition comprising an aqueous microdispersion of wax particles comprising a lipophilic hydrofluorocarbon compound, said particles being solid up to a temperature equal to at least 30° C. and said lipophilic hydrofluorocarbon compound having at least 10% to at most 90% fluorine atoms relative to the total number of fluorine and hydrogen atoms, said composition being free of perfluorinated organofluorine compounds, wherein said lipophilic hydrofluorocarbon compound has the structure of formula (III):

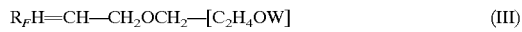

wherein:
C₂H₄OW is —CHOH—CH₂W or —CHW—CH₂OH,
W is —OR—, —SR—, —COOR, —O₆H₅ or O—C₆H₄—R',
R is an alkyl of 1 to 18 carbon atoms,
R' is —CH₃ or —OH in the ortho or para position, and
R_F is a perfluorinated alkyl radical of 4 to 20 carbon atoms.

19. The composition according to claim 18 wherein the said lipophilic hydrofluorocarbon compound is present in an amount ranging from 5% to 50% by weight relative to the total weight of said wax.

20. The composition according to claim 18 wherein said lipophilic hydrofluorocarbon compound is present in an amount ranging from 10% to 30% by weight relative to the total weight of said wax.

21. The composition according to claim 18 wherein said wax is present in an amount ranging from 1% to 40% by weight relative to the total weight of said composition.

22. The composition according to claim 18 wherein said wax is present in an amount ranging from 5% to 30% by weight relative to the total weight of said composition.

23. A process for the treatment of hair or eyelashes comprising applying the composition of claim 18 to said hair or eyelashes.

24. A process for improving the plasticity of a cosmetic microdispersion containing a wax, comprising adding a lipophilic hydrofluorocarbon compound of formula (III):

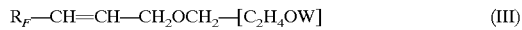

wherein:
C₂H₄OW is —CHOH—CH₂W or —CHW—CH₂OH,
W is —OR—, —SR, —COOR, —OC₆H₅ or —O—C₆H4—R'—,
R is an alkyl of 1 to 18 carbon atoms,
R' is —CH₃ or —OH in the ortho or para position, and
R_F is a perfluorinated alkyl radical of 4 to 20 carbon atoms;
said wax microdispersion being free of perfluorinated organofluorine compounds.

* * * * *